US012574474B2

(12) United States Patent
Lien et al.

(10) Patent No.:  US 12,574,474 B2
(45) Date of Patent:      Mar. 10, 2026

(54) METHOD OF ASSESSING A BIOMETRIC DURING A VIDEO CALL, AND SYSTEM IMPLEMENTING THE SAME

(71) Applicant: GRANDPAD, INC., Hopkins, MN (US)

(72) Inventors: Scott Lien, Hopkins, MN (US); David Tyler, Medford, MA (US)

(73) Assignee: GrandPad, Inc., Hopkins, MN (US)

( * ) Notice: Subject to any disclaimer, the term of this patent is extended or adjusted under 35 U.S.C. 154(b) by 196 days.

(21) Appl. No.: 18/357,249

(22) Filed: Jul. 24, 2023

(65) Prior Publication Data

US 2024/0073363 A1      Feb. 29, 2024

Related U.S. Application Data

(60) Provisional application No. 63/373,233, filed on Aug. 23, 2022.

(51) Int. Cl.
*H04N 7/14*          (2006.01)
*A61B 5/00*          (2006.01)

(52) U.S. Cl.
CPC .............. *H04N 7/147* (2013.01); *A61B 5/72* (2013.01)

(58) Field of Classification Search
CPC ................................. H04N 7/147; A61B 5/72
See application file for complete search history.

(56) References Cited

U.S. PATENT DOCUMENTS

| | | | | |
|---|---|---|---|---|
| 11,213,256 | B2 | 1/2022 | Shiue | |
| 11,589,003 | B2 * | 2/2023 | Schoenberg | ..... H04N 21/42204 |
| 2016/0088257 | A1 * | 3/2016 | Kim | ........................ G16H 10/60 |
| | | | | 348/14.07 |
| 2017/0235909 | A1 * | 8/2017 | Lozano | .................. G16H 40/20 |
| | | | | 705/3 |
| 2019/0133510 | A1 * | 5/2019 | el Kaliouby | ............ G10L 25/63 |
| 2020/0323448 | A1 | 10/2020 | Shiue | |
| 2021/0251567 | A1 | 8/2021 | Wu | |
| 2022/0086393 | A1 * | 3/2022 | Peters | .................... H04N 7/147 |
| 2023/0247169 | A1 * | 8/2023 | Garcia i Tormo | ..... A61B 5/165 |
| | | | | 348/14.03 |

OTHER PUBLICATIONS

WikipediA, 4K resolution, https://en.wikipedia.org/wiki/4K_resolution, downloaded Aug. 20, 2022, 23 pages.
WikipediA, WebRTC, https://en.wikipedia.org/wiki/WebRTC, downloaded Aug. 20, 2022, 8 pages.

* cited by examiner

*Primary Examiner* — Amal S Zenati
(74) *Attorney, Agent, or Firm* — Saul Ewing LLP; Brian R. Landry; Ian Mahany-Horton

(57)                ABSTRACT

One aspect of the invention provides a method of assessing a biometric during a video call, the method comprising the steps of: a) establishing a videotelephony connection with a remote device, the videotelephony connection including a video channel and an audio channel; b) receiving an instruction to assess a biometric; c) suspending the video channel of the videotelephony connection with the remote device; d) capturing a video stream; e) determining a biometric of a subject from the video stream; f) transmitting the biometric to the remote device; and g) reestablishing the video channel of the videotelephony connection with the remote device.

15 Claims, 16 Drawing Sheets

STEP 200:  ESTABLISH A VIDEOTELEPHONY CONNECTION WITH A REMOTE DEVICE, THE VIDEOTELEPHONY CONNECTION INCLUDING A VIDEO CHANNEL AND AN AUDIO CHANNEL

STEP 202:  RECEIVE AN INSTRUCTION TO ASSESS A BIOMETRIC

STEP 204:  DISPLAY A VISUAL DIRECTION FOR THE SUBJECT.

STEP 206:  SUSPEND THE VIDEO CHANNEL OF THE VIDEOTELEPHONY CONNECTION WITH THE REMOTE DEVICE

STEP 208:  CAPTURE A VIDEO STREAM

STEP 210:  DETERMINE A BIOMETRIC OF A SUBJECT FROM THE VIDEO STREAM

STEP 212:  VERIFY THE BIOMETRIC DETERMINED IN STEP E

STEP 214:  TRANSMIT THE BIOMETRIC TO THE REMOTE DEVICE

STEP 216:  REESTABLISH THE VIDEO CHANNEL OF THE VIDEOTELEPHONY CONNECTION WITH THE REMOTE DEVICE.

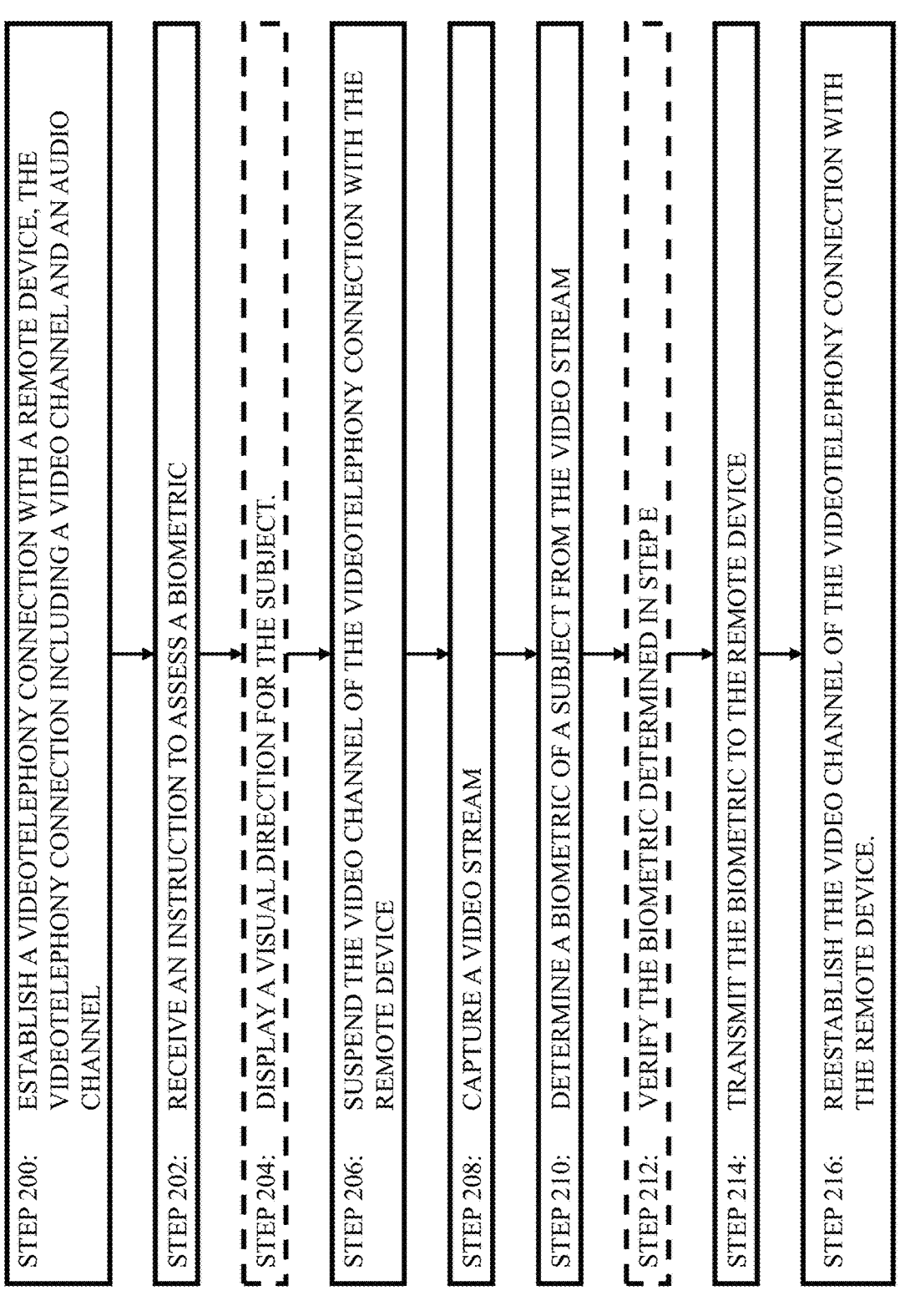

STEP 200: ESTABLISH A VIDEOTELEPHONY CONNECTION WITH A REMOTE DEVICE, THE VIDEOTELEPHONY CONNECTION INCLUDING A VIDEO CHANNEL AND AN AUDIO CHANNEL

STEP 202: RECEIVE AN INSTRUCTION TO ASSESS A BIOMETRIC

STEP 204: DISPLAY A VISUAL DIRECTION FOR THE SUBJECT.

STEP 206: SUSPEND THE VIDEO CHANNEL OF THE VIDEOTELEPHONY CONNECTION WITH THE REMOTE DEVICE

STEP 208: CAPTURE A VIDEO STREAM

STEP 210: DETERMINE A BIOMETRIC OF A SUBJECT FROM THE VIDEO STREAM

STEP 212: VERIFY THE BIOMETRIC DETERMINED IN STEP E

STEP 214: TRANSMIT THE BIOMETRIC TO THE REMOTE DEVICE

STEP 216: REESTABLISH THE VIDEO CHANNEL OF THE VIDEOTELEPHONY CONNECTION WITH THE REMOTE DEVICE.

FIG. 2

GUD 114

DEVICE 102

SUBJECT 132

REMOTE DEVICE USER 130

DEVICE 1302

PORT 1348

STAND 1350

DEVICE 1302

CHARGING STAND 1354

METHOD OF ASSESSING A BIOMETRIC DURING A VIDEO CALL, AND SYSTEM IMPLEMENTING THE SAME

CROSS-REFERENCE TO RELATED APPLICATION

This application claims the benefit of priority under 35 U.S.C. § 119(e) to U.S. Provisional Patent Application Ser. No. 63/373,233, filed Aug. 23, 2022. The entire content of the application is hereby incorporated by reference herein.

BACKGROUND OF THE INVENTION

Presently, there is growing demand for remote appointments with health professionals, especially for the elderly and vulnerable people. Taking standard vital measurements, such as blood pressure or heart rate, traditionally requires in-person examination. When such measurements are desired or required for an appointment, the need for using in-person measurement devices to take vital measurements limits the practically of remote appointments with health professionals.

SUMMARY OF THE INVENTION

One aspect of the invention provides a method of assessing a biometric during a video call, the method comprising the steps of: a) establishing a videotelephony connection with a remote device, the videotelephony connection including a video channel and an audio channel; b) receiving an instruction to assess a biometric; c) suspending the video channel of the videotelephony connection with the remote device; d) capturing a video stream; e) determining a biometric of a subject from the video stream; f) transmitting the biometric to the remote device; and g) reestablishing the video channel of the videotelephony connection with the remote device.

This aspect of the invention can have a variety of embodiments. The method can further include the step of: displaying a visual direction for the subject. The method can further include the step of: verifying the biometric determined (e.g., using another sensor).

The biometric can be selected from the group consisting of: a heart rate, a respiration rate, an oxygen saturation (SpO2), a body temperature, and a blood pressure. The video stream can be captured by a camera. The determining the biometric of the subject can use photoplethysmography.

The method can be implemented using a device selected from the group consisting of: a smartphone, a tablet computer, a laptop computer, and a general purpose computing device. The remote device can be selected from the group consisting of: another smartphone, another tablet computer, another laptop computer, and another general purpose computing device. The method can be implemented using a tablet computer.

In certain aspects, the method may be implemented using a device. The device can include a graphical user display. The device can further include a camera configured to capture the video stream. The device can further include a processor programmed to implement the method of the present disclosure.

This aspect of the invention can have a variety of embodiments. In one aspect, the device can further include one or more of a communication interface, a microphone, a memory device, and a storage device.

In certain aspects, the method may be implemented using a system. The system can include a device. The device can include a graphical user display, a camera configured to capture the video stream, and a processor configured to implement the method of the present disclosure. The system can include a remote device, the remote device being selected from the group consisting of: a smartphone, a tablet computer, a laptop computer, and a general purpose computing device.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIG. 2 depicts a flow diagram of a method of assessing a biometric during a video call, in accordance with an embodiment of the present disclosure.

DEFINITIONS

Figure 1:
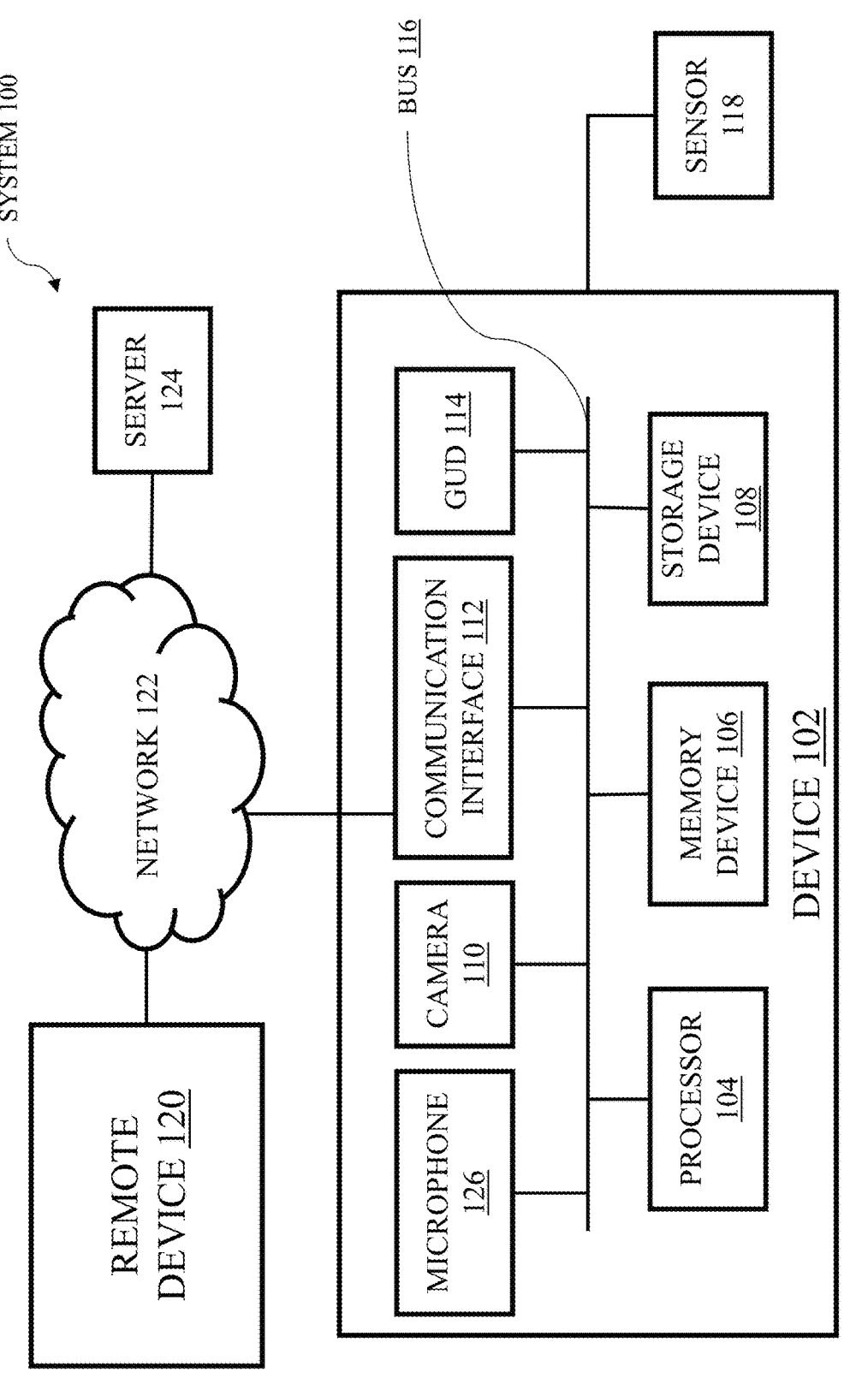
FIG. 1 depicts a network diagram, in accordance with an embodiment of the present disclosure.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, "suspension" or "suspending" means pausing, stopping, or temporarily terminating.

DETAILED DESCRIPTION OF THE INVENTION

It would be desirable to enable assessing biometrics or vital measurements during a video call.

The present disclosure provides a method of assessing a biometric during a video call. The present disclosure provides a method or utility by which a care practitioner (e.g., a nurse, doctor, another health professional, etc.) in one location using a device accessing a computer application can connect to another device (e.g., a computer, a tablet, a smartphone, etc.) at another location where a subject is located. The care practitioner may execute computer-implement processes, such as: communicate with a subject (e.g., via voice call, video call, videotelephony communication, etc.); inform the subject that biometric or a vital sign measurement (e.g., heart rate, respiration rate, blood pressure, etc.) will be taken; initiate or cause the biometric or vital sign measurement to take place by executing an application on the another device remote computer and then retrieve the biometric or vital sign measurement; review the biometric or vital sign measurement; store the biometric or vital sign measurement of the subject (and related subject information) for future reference (e.g., to track the progression of the subjects condition, to determine whether in-person treatment is appropriate, etc.).

Remote Photoplethysmography (rPPG) can be used to measure biometrics (or vital signs) including heart rate and blood pressure. As implemented on a device such as a tablet, rPPG utilizes a high resolution camera to capture multiple images of the subject and executes a machine learning model that detects the changes in the face images to determine the vital sign measurements.

Referring now to the drawings, FIG. 1 illustrates a block diagram of system 100. System 100 includes device 102 (e.g., a local device, a personal device, smartphone, a tablet computer, a laptop computer, and a general purpose computing device, etc.) and remote device 120. Device 102 is illustrated communicably coupled to remote device via network 122 (e.g., an internet connection, a cloud-based connection, a telecommunication tower, a cellular connection, etc.). In certain embodiments, a server 124 (e.g., an external server, a processing server, a cloud-computing server, etc.) can be integrated with network 122 (e.g., for data computation, request configuration, account verification, etc.).

Device 102 can include a processor 104, a memory device 106, a storage device 108, a camera 110, a communication interface 112, a graphical user display (GUD) 114, a microphone 126, and/or a bus 116. Device 102 can include a sensor 118 (e.g., an IR scanner, an external blood pressure monitoring device, etc.).

Processor 104 can be any type of processing device (e.g., a central processing unit (CPU), graphical processing unit (GPU), etc.) for carrying out instructions, processing data, and so forth. The processor can implement an operating system such as ANDROID™ or IOS®.

Memory device 106 can be any type of memory device including any one or more of random access memory (RAM), read-only memory (ROM), flash memory, electrically erasable programmable read only memory (EEPROM), and so forth.

Storage device 108 can be any data storage device for reading/writing from/to any removable and/or integrated optical, magnetic, and/or optical-magneto storage medium, and the like (e.g., a hard disk, a SSD, a compact disk read-only memory (CD-ROM), CD-ReWritable (CDRW), digital versatile disc-ROM (DVD-ROM), DVD-RW, and so forth). Storage device 108 can also include a controller/ interface for connecting to the system bus 116. Thus, memory device 106 and storage device 108 are suitable for storing data as well as instructions for programmed processes for execution of processor 104.

Camera 110 can be (or include) a high-resolution camera, a high-frame-rate camera, a webcam, a camera integrated into a tablet, a camera integrated into a cell phone, a camera integrated into a personal device, a camera integrated into a computer, or any other device with the capability. Camera 110 can be reconfigured in accordance with camera capture settings, as desired for certain biometric analyses. For example, in certain applications, the camera capture settings may be reconfigured in applications desiring: low latency, certain frame rates (e.g., 30 frames per second), certain color-saturation settings, certain lighting conditions, etc. Camera 110 can optionally include an infrared sensor to facilitate measurement of $SpO_2$ and/or body temperature.

Microphone 126 can be (or include) any device capable of capturing or recording sound in connection with a videotelephony call. Microphone 126 can be integrated directly into device 102 or configured to externally connect (e.g., physically, via wireless transmission, etc.) to device 102 (or any component therein).

GUD 114 can include a touch screen, which can also provide input. Other inputs can include, a keyboard, a keypad, a mouse, a trackpad, or any other type of interface, which can be connected to the system bus 116 (e.g., through a corresponding input/output device interface/adapter).

Communication interface 112 can be adapted and configured to communicate with any type of external device (e.g., remote device 120, an external sensor, etc.) or with other components of device 102 (e.g., camera 110, microphone 126, GUD 114, etc.). Communication interface 112 can implement various wired or wireless protocols (e.g., WI-FI®, BLUETOOTH®, LTE, DSRC or other suitable communication protocol).

In certain embodiments, device 102 can be configured such that it is discoverable by remote device 120. For example, device 102 can be registered in a database of server 124 such that it is identified to a particular user. By implementing a permission-based model such that all devices are known, communications between remote device 120 and device 102 is more secure (e.g., by preventing unvetted communications) and easy to begin using device 102.

Referring now to FIG. 2, a flow diagram depicting a method of assessing a biometric during a video call is illustrated, in accordance with exemplary embodiments of the present disclosure. As is understood by those skilled in the art, certain steps included in the flow diagram may be omitted; certain additional steps may be added; and the order of the steps may be altered from the order illustrated. FIG. 2 may be better or further described in connection with FIGS. 3-12, as appropriate.

In Step 200, a videotelephony connection, including a video channel and an audio channel, is established with a remote device (e.g., remote device 120). For example, the videotelephony connection may be established between device 102 (e.g., a local device, such as a tablet computer of an elderly user) and remote device 120 (e.g., a desktop computer of a remote service provider, such as a nurse). The videotelephony connection can be initiated from device 102 or from remote device 120 and the like. In some embodiments (e.g., if a user has given consent), the videotelephony connection can be initiated remotely (e.g., after a set period of audible and/or visual alerts) without the need for the user to interact with the device 102. This can be particularly useful if the user has limited mobility or dexterity.

Figure 3:
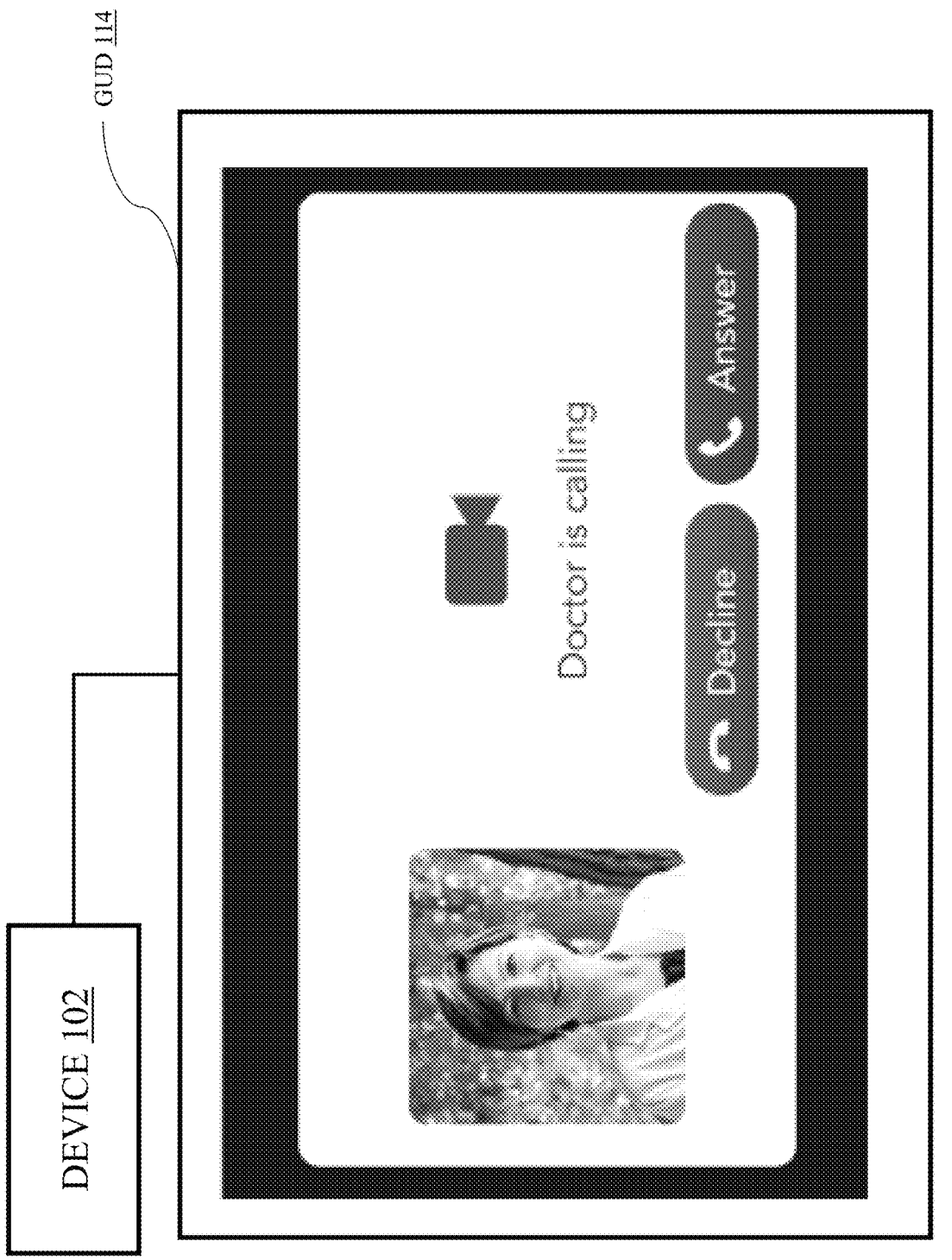
FIGS. 3-12 depict screenshots displayed in accordance with carrying out certain steps of an embodiment of the present disclosure.
Figure 4:
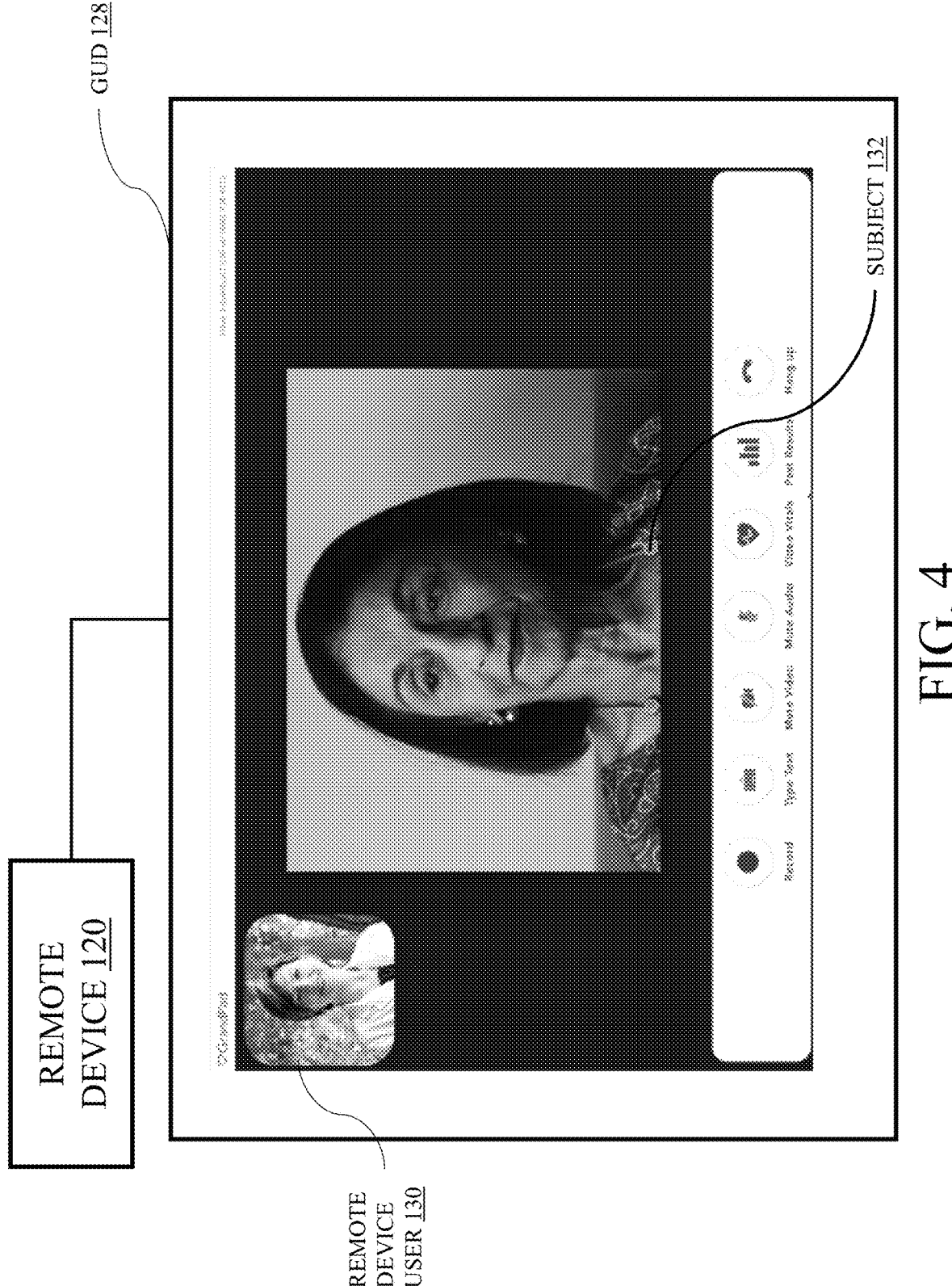
Figure 5:
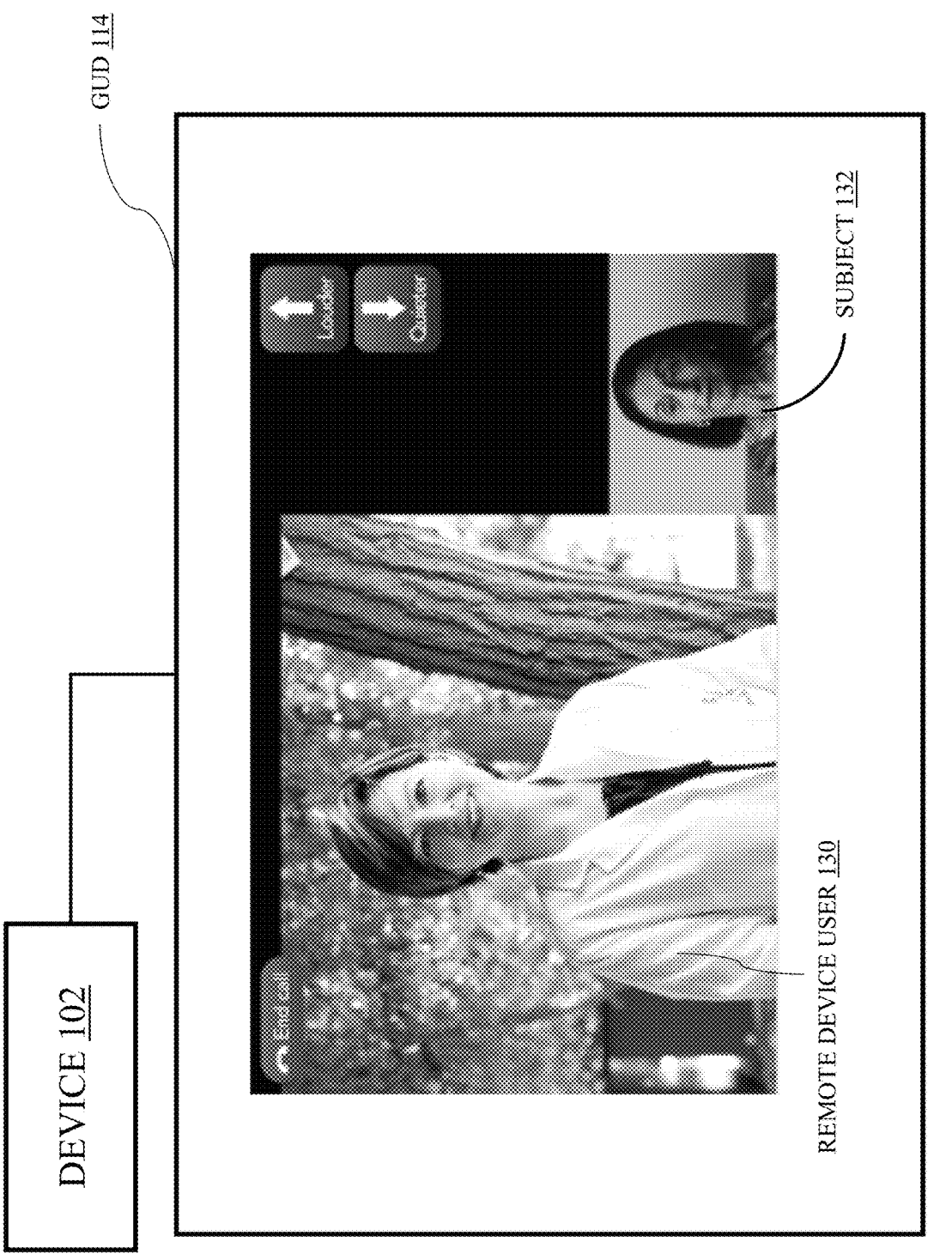

As illustrated in FIG. 3, GUD 114 of device 102 is in a state prior to completing Step 200. As illustrated in FIG. 4, GUD 128 of remote device 120 is in a state after Step 200 has been completed. Here, a remote device user 130 (e.g., a care practitioner, a doctor, a nurse, another health professional, etc.) is in a video call with subject 132 (e.g., a patient). Similarly, as illustrated in FIG. 5, GUD 114 of device 102 illustrates subject 132 in a video call with remote device user 130.

The videotelephony connection can be utilize a variety of protocols such was WebRTC (available at webrtc.googlesource.com) and/or protocols and/or services provided by OpenTalk of Berlin, Germany; Twillio of San Francisco, Californian; Vonage of Holmdel, New Jersey; and the like.

Figure 6:
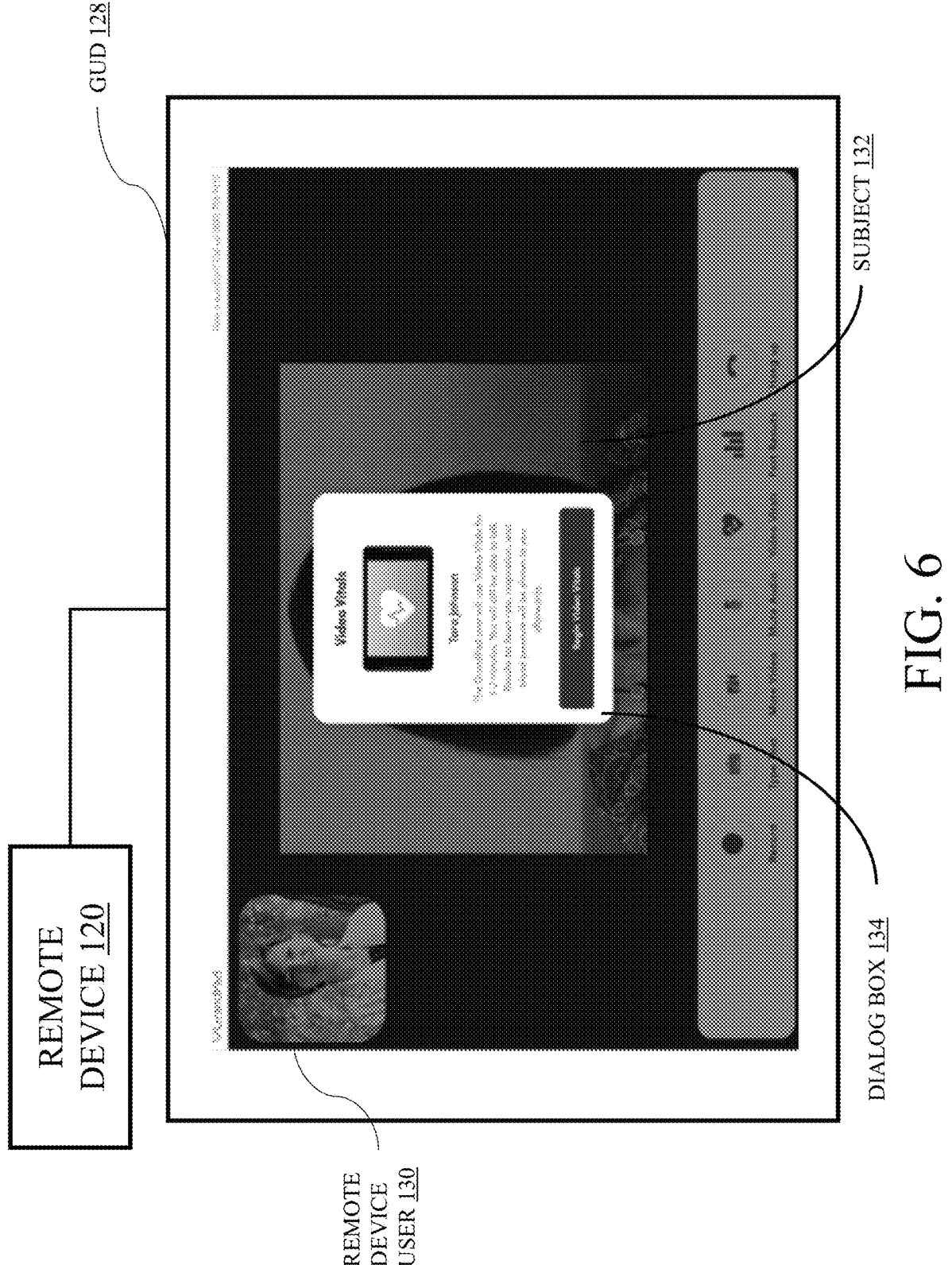
Figure 7:
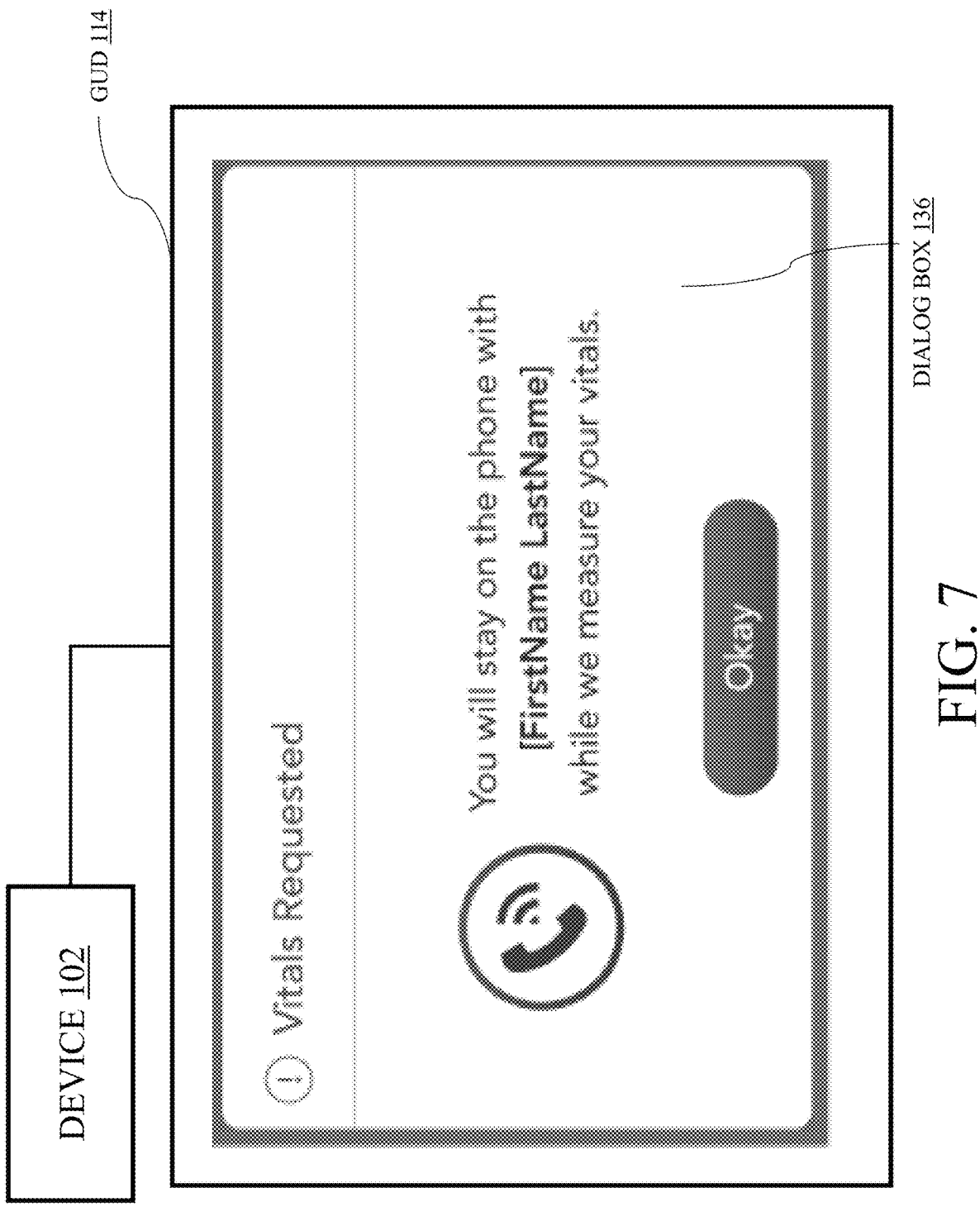

In Step 202, an instruction to assess a biometric is received. Such an instruction may be initiated by remote device user 130 or another user in communication with remote device 120. This instruction can be sent outside of the videotelephony connection, e.g., via a web socket. As illustrated in FIG. 6, GUD 128 is displaying a dialog box 134 prior to Step 202 being completed (i.e., after an instruction to assess a biometric is received). As illustrated in FIG. 7, GUD 114 is displaying a dialog box 136 after Step 202 is completed.

Figure 8:
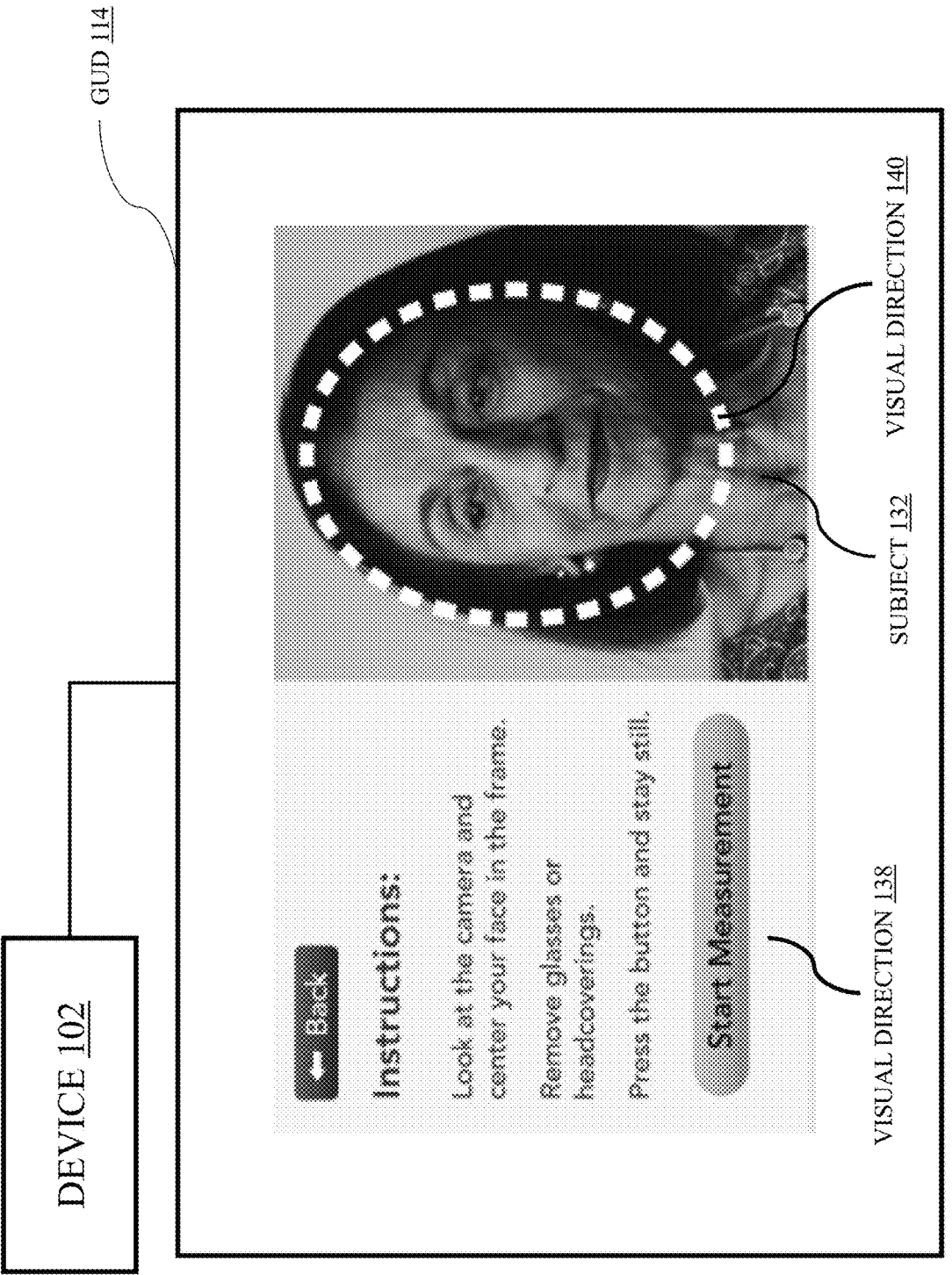

In Step 204, a visual direction for the subject is displayed. As illustrated in FIG. 8, GUD 114 is displaying visual direction 138 (i.e., a text-based direction) and visual direction 140 (i.e., a shape-based direction for positioning subject 132).

Figure 9:
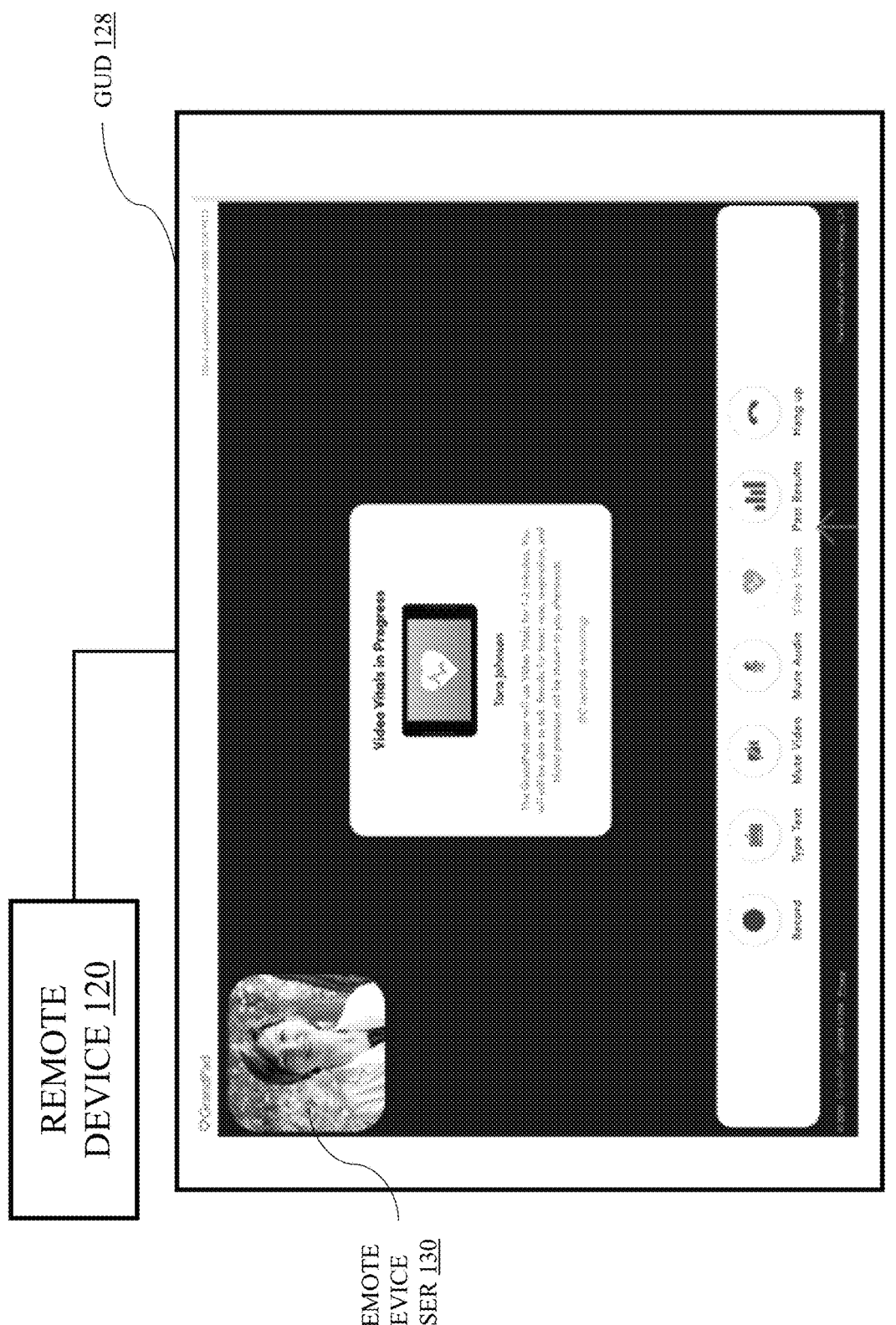

In Step 206, the video channel of the videotelephony connection with the remote device is suspended. As illustrated in FIGS. 7-9, the video channel of the videotelephony connection has been suspended (e.g., the video feed depicting the remote user has been suspended). This advantageously allows the processor 104 to prioritize any computationally intensive biometric calculations and avoids the need to steam high-quality video to a remote server for biometric calculations. Other background processes (e.g., e-mail, news, and the like) can be suspended. Maintaining the audio channel can make the biometric measurement more comfortable for the user and avoid the need to completely reestablish a conversation with between the user and the caregiver.

In Step 208, a video stream is captured. The camera 110 can first be reconfigured to capture video with a desired setting of low latency, certain frame rates (e.g., 30 frames per second), certain resolution (e.g., 4K), certain color-saturation, lighting, and the like.

Figure 10:
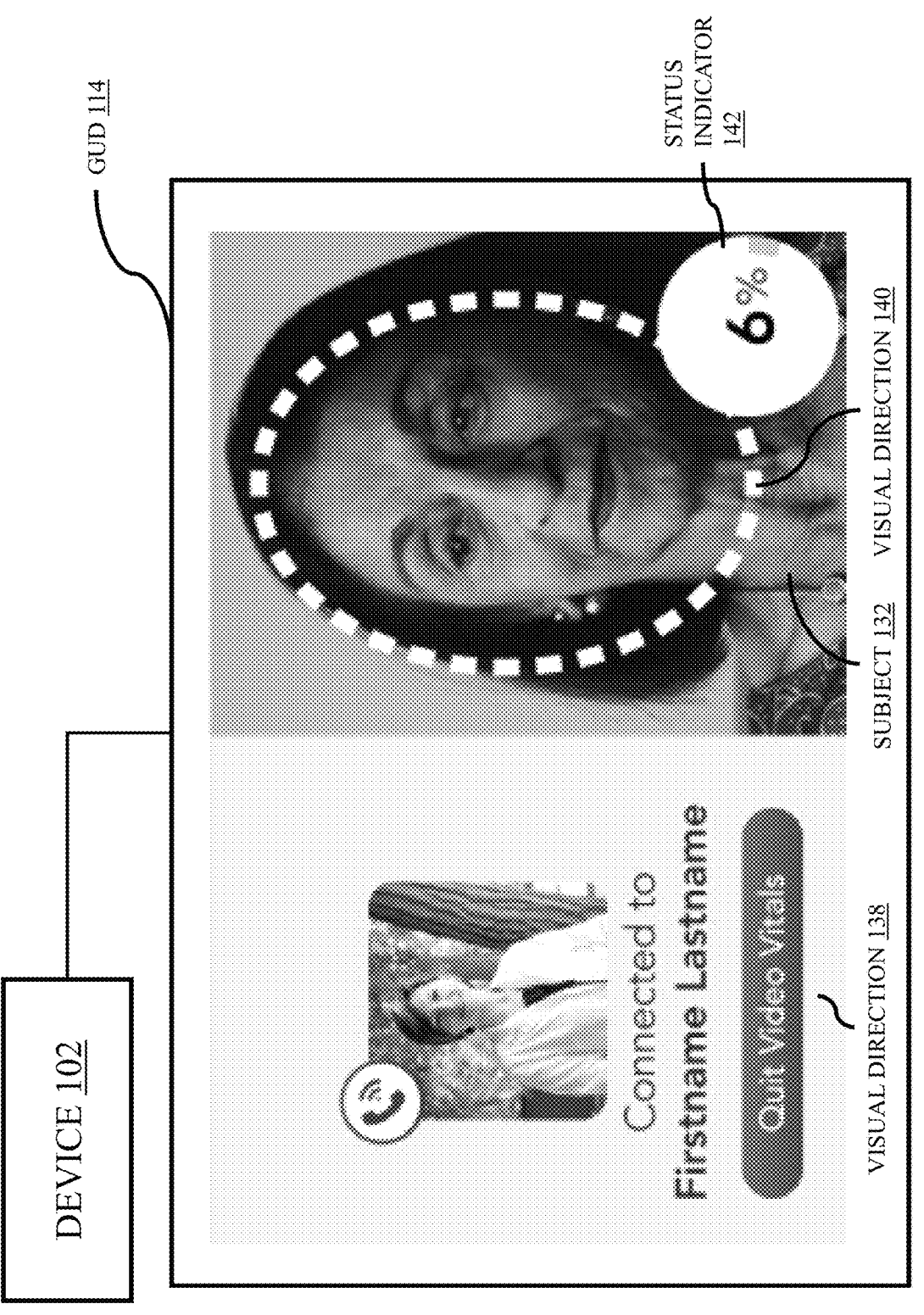

As illustrated in FIG. 10, video stream of subject 132 is being continuously captured. The video stream can be analyzed (e.g., on device 102 using processor 104 in connection with a machine learning algorithm) to determine a biometric (e.g., blood pressure, heart rate, respiration rate, oxygen saturation (SpO2), a body temperature, etc.). The analysis can be in parallel with capture or at the end of video capture. Status indicator 142 is illustrated displaying the progress of the video steam and/or the analysis. The status indicator 142 can reflect the percentage of required video that has been captured (e.g., x % of y seconds of video). In some embodiments, the required video capture can be between about 10 seconds and about 60 seconds. The processor 104 can be programmed to perform pre-processing, e.g., to ensure sufficient lighting, stillness of the subject, and the like.

In Step 210, a biometric (e.g., biometrics 144 of FIG. 11) of a subject is determined from the video stream. The biometric of the subject can be determined using photoplethysmography. In step 212, the biometric determined in Step 210 can be verified (e.g., a blood pressure reading may be independently verified using an external blood pressure measuring device, an external heartrate measuring device, etc.).

One or more biometrics can be calculated using software and/or hardware local to device 102. Suitable software is available from FaceHeart Corporation of Taipei, Taiwan and is described in U.S. Pat. No. 11,213,256 of U.S. Patent Application Publication Nos. 2020/0323448 and 2021/0251567.

Figure 11:
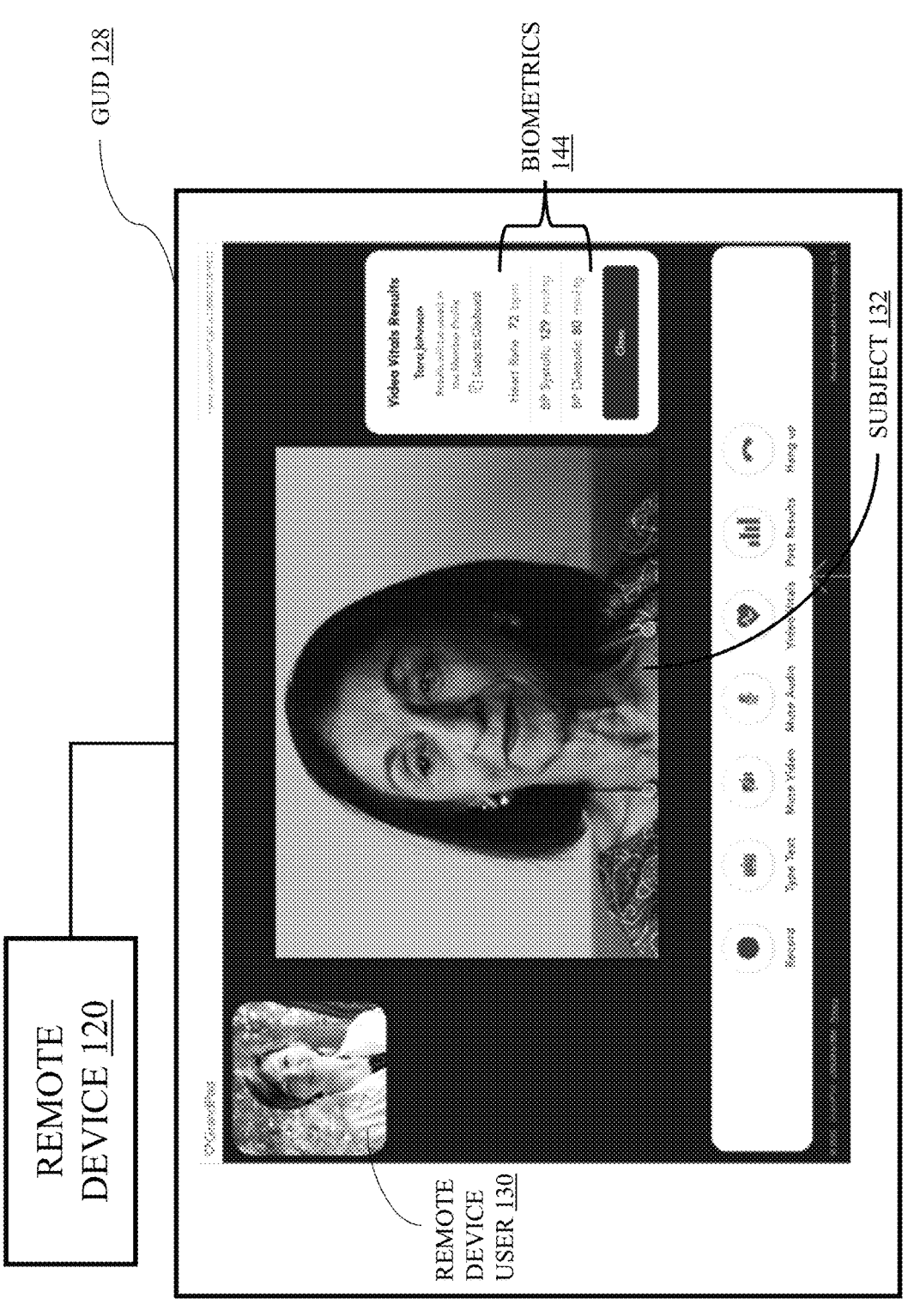
Figure 12:
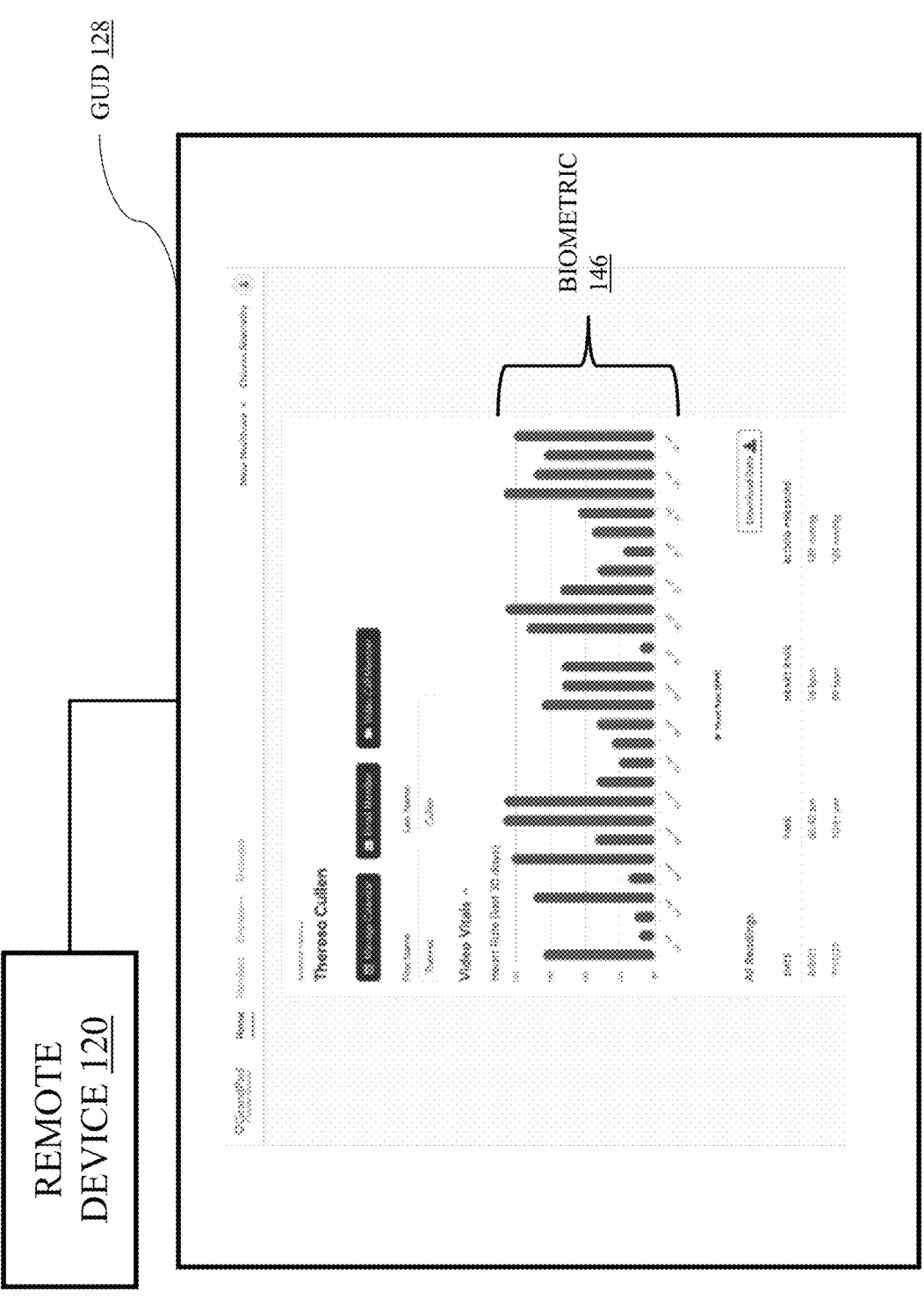

In Step 214, the biometric is transmitted to the remote device. In Step 216, the video channel of the videotelephony connection is reestablished with the remote device. As illustrated in FIG. 11, steps 214 and 216 have been completed; the transmitted biometrics 144 and the video channel displaying subject 132 are being displayed on GUD 128 to remote device user 130. FIG. 12 illustrates a plurality of biometrics 146 (i.e., heartrate) collected over a period of time.

Figure 13A:
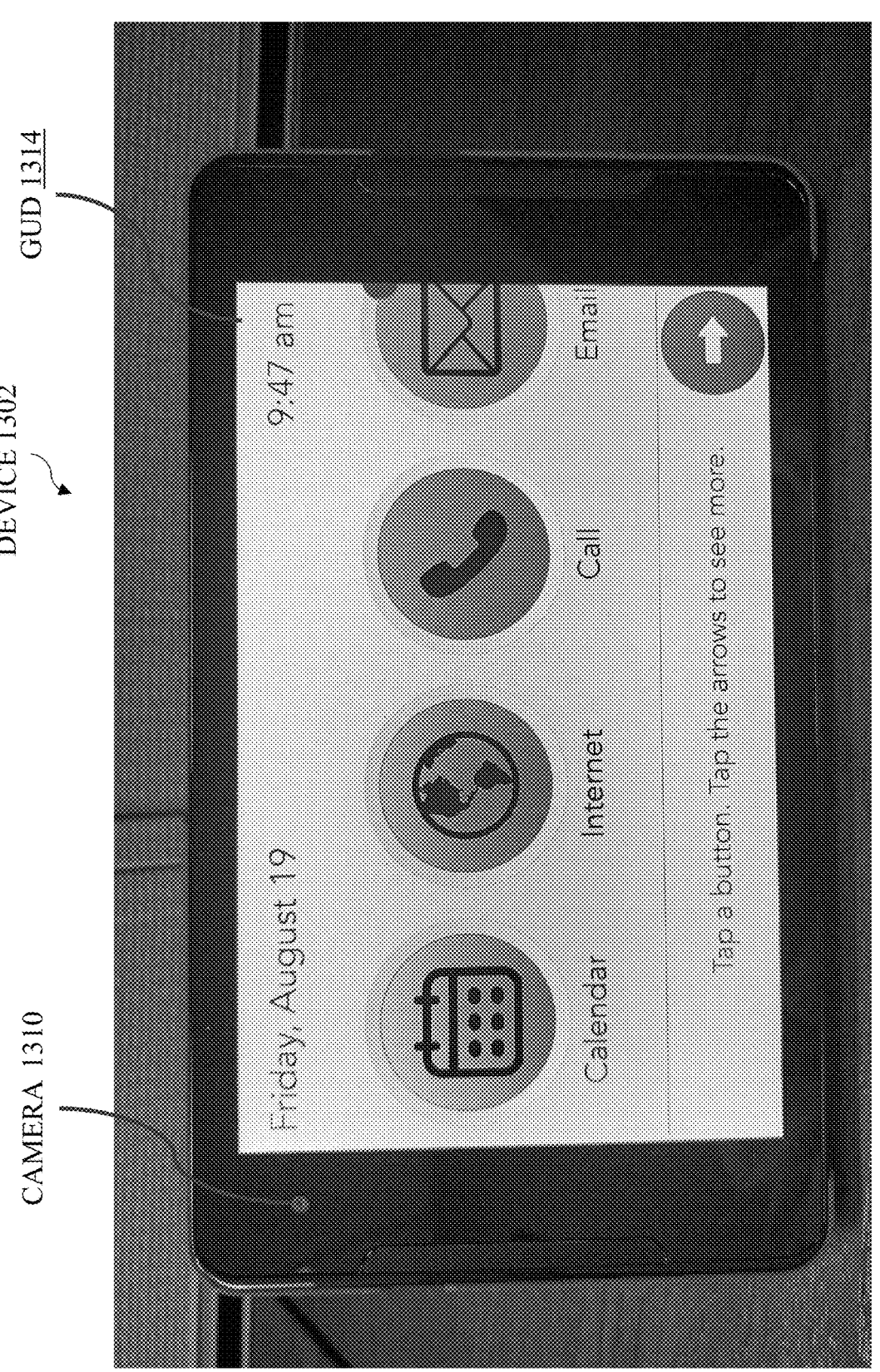
FIG. 13A-13D depict a device in accordance with an exemplary embodiment of the the present disclosure.

Referring now to FIGS. 13A-13D, a device 1302 used to assess the biometric during the video call is illustrated. Device 1302 is an embodiment of device 102 described herein. Referring specifically to FIG. 13A, a front view of device 1302 is illustrated. Device 1302 is a tablet device, including a camera 1310 (e.g., a high-resolution camera facing toward a subject in ordinary use). Camera 1310 can be used to capture a video stream of a subject in connection with determining a biometric. Camera 1310 can be used in connection with certain camera capture settings, in accordance with certain video capture applications. Device 1302 and camera 1310 are configured to determine the biometric of the subject using photoplethysmography. Device 1302 includes a graphical user display (GUD) 1314 (e.g., a touchscreen), configured to display a graphical user interface, the graphical user interface being configured to minimize the input from the subject. Further, the GUI is configured for ease of use by a subject (e.g., an elderly subject). As illustrated, device 1302 includes large icons on the graphical user interface (GUI).

Figure 13B:
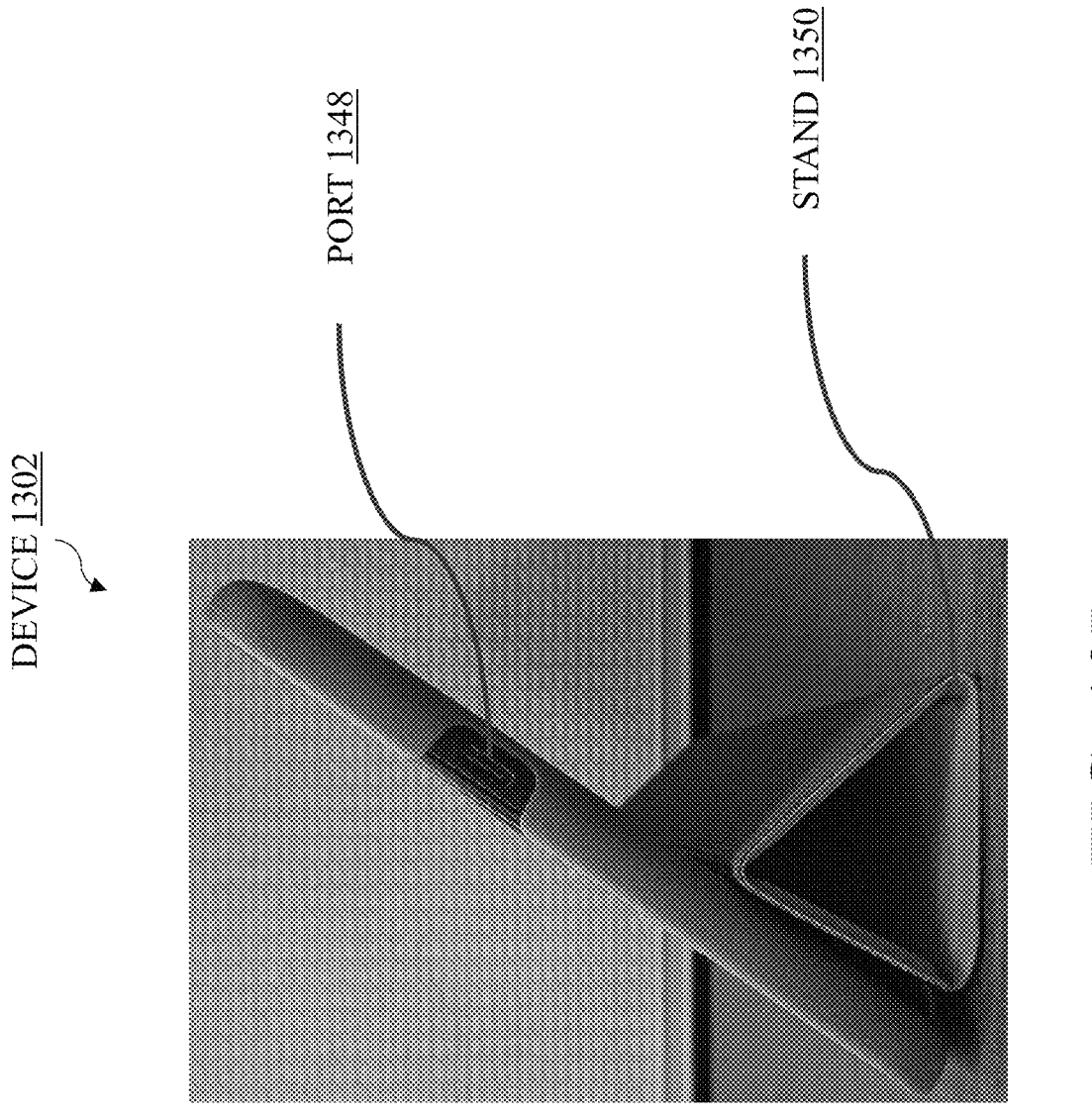

Referring now to FIG. 13B, a side view of device 1302 is illustrated. Device 1302 includes port 1348, which may be used in a charging operation, a data transfer operation, and so forth. Device 1302 includes stand 1350, which is illustrated as a foldable, segmented stand that can also be used as a cover. Stand 1350 is configured to a desired angle such that device 1302 can determine certain biometrics of the subject (e.g., using photoplethysmography).

Figure 13C:

Referring now to FIG. 13C, a rear view of device 1302 is illustrated. Device 1302 includes microphone 1226. Device 1302 also includes another camera 1252, which can be used by a subject to take pictures away from the subject.

Figure 13D:

Referring now to FIG. 13D, a front view of device 1302 mounted in a charging stand 1354 is illustrated. Charging stand 1354 may be used to wirelessly charge device 1302.

Although the invention is illustrated and described herein with reference to specific embodiments, the invention is not intended to be limited to the details shown. Rather, various modifications may be made in the details within the scope and range of equivalents of the claims and without departing from the invention.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A method of assessing a biometric during a video call, the method comprising the steps of:
   (a) establishing a videotelephony connection with a remote device, the videotelephony connection including a video channel and an audio channel;
   (b) receiving an instruction to assess a biometric;
   (c) suspending the video channel of the videotelephony connection with the remote device;
   (d) displaying a visual direction for a subject that is superimposed over a video feed of the subject;
   (e) capturing a video stream;
   (f) determining a biometric of a subject from the video stream;
   (g) transmitting the biometric to the remote device; and
   (h) reestablishing the video channel of the videotelephony connection with the remote device.

2. The method of claim 1, wherein the biometric is selected from the group consisting of: a heart rate, a respiration rate, an oxygen saturation (SpO2), a body temperature, and a blood pressure.

3. The method of claim 1, further comprising the step of:
   (i) verifying the accuracy of the biometric determined in step f.

4. The method of claim 3, wherein the verifying of step i includes using a sensor.

5. The method of claim 1, wherein the video stream is captured by a camera.

6. The method of claim 1, wherein the determining the biometric of the subject uses photoplethysmography.

7. The method of claim 1, wherein the method is implemented using a device selected from the group consisting of:

a smartphone, a tablet computer, a laptop computer, and a general purpose computing device.

8. The method of claim 7, wherein the remote device is selected from the group consisting of: another smartphone, another tablet computer, another laptop computer, and another general purpose computing device.

9. The method of claim 1, wherein the method is implemented using a tablet computer.

10. A device used to assess the biometric during the video call using the method of claim 1, the device comprising:
   a graphical user display;
   a camera configured to capture the video stream; and
   a processor, the processor programmed to implement the method of claim 1.

11. The device of claim 10, further comprising one or more selected from the group consisting of: a communication interface, a microphone, a memory device, and a storage device.

12. The device of claim 10, wherein the graphical user display is configured to display a graphical user interface, the graphical user interface being configured to minimize the input from the subject.

13. The device of claim 10, wherein the device is configured to determine the biometric of the subject using photoplethysmography.

14. The device of claim 10, wherein the biometric is selected from the group consisting of: a heart rate, a respiration rate, an oxygen saturation (SpO2), a body temperature, and a blood pressure.

15. A system used to assess the biometric during the video call using the method of claim 1, the system comprising:
   a device including:
      a graphical user display;
      a camera configured to capture the video stream; and
      a processor, the processor configured to implement the method of claim 1; and
   the remote device, the remote device being selected from the group consisting of: a smartphone, a tablet computer, a laptop computer, and a general purpose computing device.

* * * * *